US009585903B2

(12) United States Patent
Prabhune et al.

(10) Patent No.: US 9,585,903 B2
(45) Date of Patent: Mar. 7, 2017

(54) PHARMACEUTICAL COMPOSITION COMPRISING SOPHOROLIPID IN COMBINATION WITH AN ANTIBIOTIC

(71) Applicant: Council of Scientific & Industrial Research, New Delhi (IN)

(72) Inventors: Asmita Ashutosh Prabhune, Pune (IN); Kasturi Joshi-Navare, Pune (IN)

(73) Assignee: Council of Scientific & Industrial Research, New Dehli (IN)

( * ) Notice: Subject to any disclaimer, the term of this patent is extended or adjusted under 35 U.S.C. 154(b) by 123 days.

(21) Appl. No.: 14/449,320

(22) Filed: Aug. 1, 2014

(65) Prior Publication Data

US 2015/0094273 A1 Apr. 2, 2015

(30) Foreign Application Priority Data

Sep. 30, 2013 (IN) .......................... 2888/DEL/2013

(51) Int. Cl.
| | |
|---|---|
| *A61K 31/7024* | (2006.01) |
| *A61K 31/7028* | (2006.01) |
| *C07H 15/04* | (2006.01) |
| *A61K 31/65* | (2006.01) |
| *A61K 31/545* | (2006.01) |
| *A61K 45/06* | (2006.01) |

(52) U.S. Cl.
CPC ........ *A61K 31/7028* (2013.01); *A61K 31/545* (2013.01); *A61K 31/65* (2013.01); *A61K 31/7024* (2013.01); *A61K 45/06* (2013.01); *C07H 15/04* (2013.01)

(58) Field of Classification Search
None
See application file for complete search history.

(56) References Cited

PUBLICATIONS

Purdy et al., "Acne Vulgaris" Clinical Evidence (2010) pp. 1-71.*
Ashby et al., "Biopolymer scaffolds for use in delivering antimicrobial sophorolipids to the acne-causing bacterium Propionibacterium acnes" New Biotechnology (2011) vol. 28 No. 1 pp. 24-30.*
Adwan, Ghaleb et al., Synergistic Effects of Plant Extracts and Antibiotics on Staphylococcus aureus Strains Isolated from Clinical Specimens, Middle-East Journal of Scientific Research 3 (3): 2008, pp. 134-139.
Aiyegoro, Olayinka et al., Interactions of Antibiotics and Methanolic Crude Extracts of Afzelia Africana (Smith.) Against Drug Resistance Bacterial Isolates, International Journal of Molecular Sciences, 2011, 12, pp. 4477-4487.
Alanis, Alfonso J., Resistance to Antibiotics: Are We in the Post-Antibiotic Era?, Archives of Medical Research 36, (2005), pp. 697-705.
Allahverdiyev, Adil M., et al., Antileishmanial effect of silver nanoparticles and their enhanced antiparasitic activity under ultraviolet light, International Journal of Nanomedicine, 2011:6, pp. 2705-2714.
Azim, Himanshu et al., Candida antarctica Lipase B-Catalyzed Synthesis of Poly(butylene succinate): Shorter Chain Building Blocks Also Work, Biomacromolecules, 2006, vol. 7, pp. 3093-3097.
Bisht, Kirpal et al., Enzyme-Mediated Regioselective Acylations of Sophorolipids, J. Org. Chem., 1999, vol. 64, pp. 780-789.
Van Bogaert, Inge N.A. et al., Microbial production and application of sophorolipids, Appl. Microbiol Biotechnol, 2007, 76, pp. 23-34.
Englander, Laura MD et al., Nitric Oxide Nanoparticle Technology a Novel Antimicrobial Agent in the Context of Current Treatment of Skin and Soft Tissue Infection, The Journal of Clinical and Aesthetic Dermatology, Jun. 2010, vol. 3, No. 6, pp. 45-50.
Gupta, Reetika, Biosynthesis of novel Sophorolipids using Candida bombicola ATCC 22214: Characterization and applications, A Thesis submitted by Reetika Gupta, The University of Pune, Division of Biochemical Sciences National Chemical Laboratory, Pune, India, Jun. 2012, 176 pgs.
Gutmann, Laurent MD et al., The Possible Role of Prins in Bacterial Antibiotic Resistance, Ann Intern Med., 1984; 101(4): pp. 544-557.
Hu, Yongmei et al., Sophorolipid production from different lipid precursors observed with LC-MS, Enzyme and Microbial Technology, 2001, vol. 29, pp. 593-601.
Inoh, Yoshikazu et al., Biosurfactants of MEL-A Increase Gene Transfection Mediated by Cationic Liposomes, Biochemical and Biophysical Research Communications, 2001, 289, pp. 57-61.
Kaper, James B. et al., Pathogenic *Escherichia coli*, Nature Reviews/Microbiology, Feb. 2004, vol. 2, pp. 123-140.
Joshi-Navare, Kasturi et al., Differentiation-inducing ability of sophorolipids of oleic and linoleic acids using a glioma cell line, Biotechnology Jounal, 2011, vol. 6, pp. 509-512.
Levy, Stuart B. et al., Antibacterial resistance worldwide: causes, challenges and responses, Nature Medicine Supplement, Dec. 2004, vol. 10, No. 12, pp. S122-S129.
Bolla, Jean-Michel et al., Strategies for bypassing the membrane barrier in multidrug resistant Gram-negative bacteria, EEBS Letters 585, 2011, pp. 1682-1690.
Rai, Akhilesh et al., Antibiotic mediated synthesis of gold nanoparticles with potent antimicrobial activity and their application in antimicrobial coatings, Journal of Materials Chemistry, 2010, 20, pp. 6789-6798.
Rossolini, Gian Maria et al., Coping with antibiotic resistance: contributions from genomics, BioMed Central Ltd., Rossolini and Thaller Genome Medicine 2010, 2:15, pp. 1-5.
Singh, Pooja et al., Potential applications of microbial surfactants in biomedical sciences, Trends in Biotechnology, Mar. 2004, vol. 22, No. 3, pp. 142-146.

(Continued)

*Primary Examiner* — Eric Olson
(74) *Attorney, Agent, or Firm* — McDonald Hopkins LLC

(57) ABSTRACT

The invention discloses synergistic pharmaceutical composition comprising an antibiotic and sophorolipid, to effectively combat the problem of antibiotic resistance by increasing the permeability of the antibiotic drugs across the outer membrane of bacteria. The sophorolipid being amphiphilic in nature can span through the structurally alike cell membrane and facilitate the entry of antibiotic drug molecules.

9 Claims, 4 Drawing Sheets

(56) References Cited

PUBLICATIONS

Figure 1:
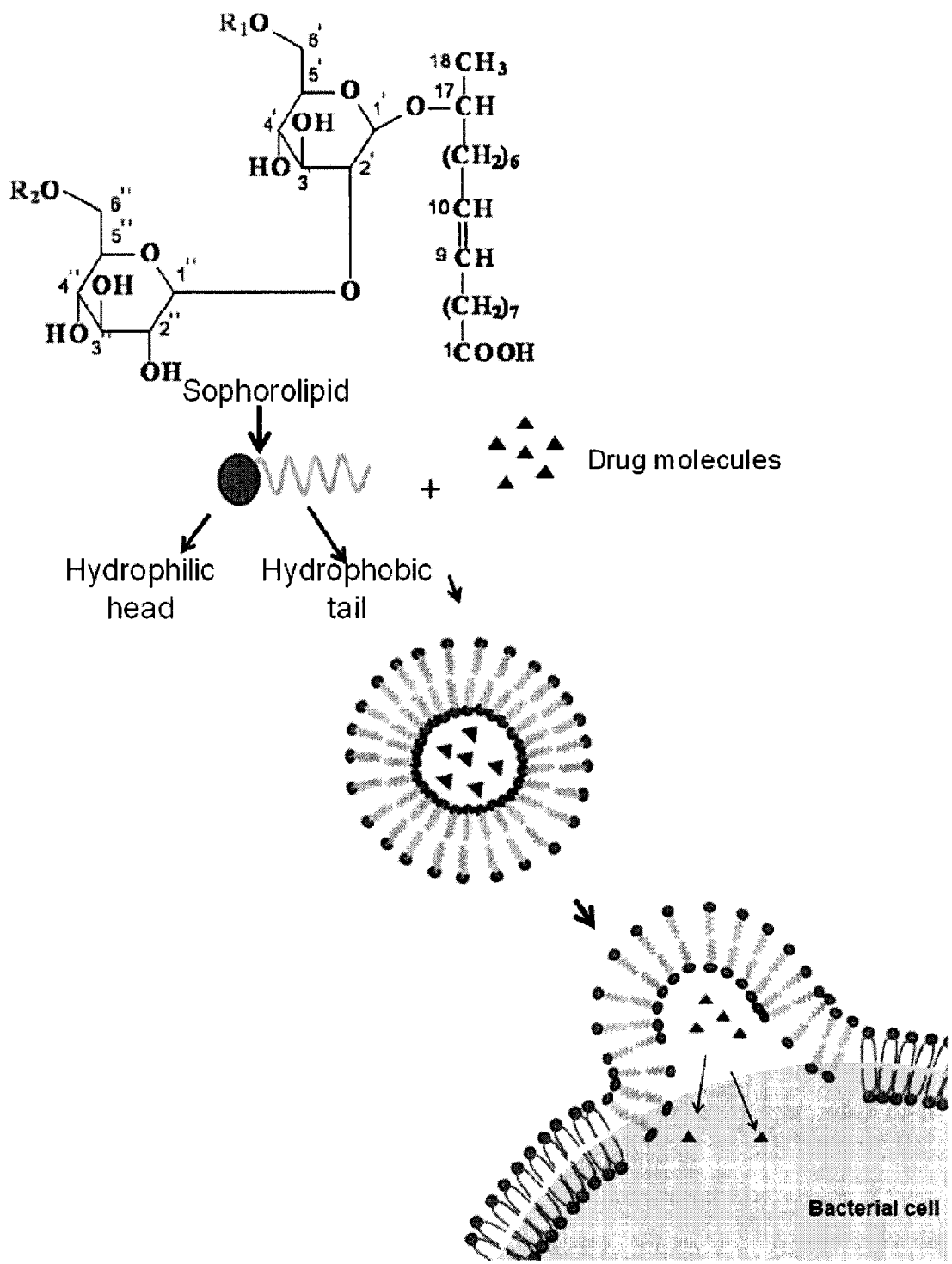

Sleiman, Joseph et al., Sophorolipids as Antibacterial Agents, Annals of Clinical & Laboratory Science, 2009, vol. 39, No. 1, pp. 60-63.
Sun, Xiao-Xia, Synergistic effect of sophorolipid and loess combination in harmful algal blooms mitigation, Marine Pollution Bulletin 48, 2004, pp. 863-872.
Zhang, Jinxin et al., Vegetable oil enhances sophorolipid production by *Rhodotorula bogoriensis*, Biotechnol Letter, 2011, 33, pp. 2417-2423.

* cited by examiner

PHARMACEUTICAL COMPOSITION COMPRISING SOPHOROLIPID IN COMBINATION WITH AN ANTIBIOTIC

FIELD OF THE INVENTION

This application claims priority to Indian Patent Application No. 2888/DEL/2013, filed on Sep. 30, 2013 by Council of Scientific & Industrial Research and entitled "Pharmaceutical Composition Comprising Sophorolipid in Combination with an Antibiotic", which is incorporated herein by reference in its entirety.

BACKGROUND OF THE INVENTION

The advent of antibiotics for treating bacterial infections is considered as one of the major advances in modern medicine. However, compared with other drugs, the lifetime of antibiotics for clinical use has been substantially limited by the phenomenon of antibiotic resistance (Rossolini and Thaller 2010). Owing to the use and misuse of antimicrobials during past decades, majority of clinically important bacteria have developed multiple antibiotics resistance. Such infections are severe, difficult to manage and require longer and more complex treatments (Levy and Marshall 2004; Aiyegoro et al. 2011; Alanis 2005). In this scenario, it is imperative to develop new antimicrobials or new practices of delivery that are effective for the treatment of infectious diseases caused by drug-resistant microorganisms (Aiyegoro et al. 2011).

To overcome the problem of antibiotic resistance, the approaches such as nanotechnology, genomics are being developed (Allahverdiyev et al. 2011; Rossolini and Thaller 2010). However, these approaches require detailed study for each drug, response by the target organism and are specific in nature. Combined antibiotic therapy is an alternative approach which is being practiced against Tuberculosis for over fifty years involving the drugs with different modes of action (Englander and Friedman 2010). Based on this approach, the drug synergism between antibiotics and bioactive plant extracts has also been demonstrated (Adwan and Mhanna, 2008).

Further, biosurfactants are coming up as emerging class of biomedical compounds that are suitable alternative to synthetic medicines and antimicrobial agents, and could be used as safe and effective therapeutic agents or probiotics, especially at a time when drug resistance among causal organisms for many life-threatening diseases is on the rise (Singh and Cameotra 2004). Sophorolipid (SL) is a promising candidate for such applications being produced by non pathogenic yeasts, such as *Candida bombicola, Candida apicola* and *Candida bogoriensis*. They are generally present in the form of disaccharide sophoroses (2-O-β-D-glucopyranosyl-D-glucopyranose) linked β glycosidically to the hydroxyl group at the penultimate carbon of fatty acids (Bisht et al. 1999). These SLs possesses not only antimicrobial action but also act as antifungal, antialgal, antimycoplasma and antiviral agents (Van Bogaert et al. 2007). The proposed primary mechanism of action of these surfactants is membrane lipid order perturbation, which compromises the viability of microorganisms (Azim A et al. 2006). Moreover SLs offer the advantages of biodegradability, low ecotoxicity and the production based on renewable-resource substrates. The US FDA has also approved biosurfactants/sugar esters for the use in food and pharmaceuticals. SLs are not irritating to the skin, do not trigger allergic reactions and have an oral safety level which is greater than or equal to 5 mL/kg weight. Cytotoxicity was evaluated with human epidermal keratinocytes and was proven to be low (Van Bogaert et al. 2011).

Sun, X. et al., 2004 have demonstrated the synergistic effects of combination of SL and loess for harmful algal bloom mitigation to bring down the effective dose of both when used individually (Sun et al. 2004). MannosylErythritol Lipid-A, a type of glycolipidic biosurfactant containing cationic liposomes promoted the gene transfection efficiency five to seven times with mammalian cultured cells (Inoh et al. 2001).

Antibiotic agents are thought to diffuse freely through the cell wall of gram-positive bacteria. However, in gram-negative bacteria the diffusion of a given antibiotic agent depends on the permeability of the outer membrane. This permeability is determined by the particular structure of the membrane, which is composed of proteins and an asymmetric lipid bilayer (Gutmann et al. 1984). The outer membrane of bacteria contains various protein channels, called porins, which are involved in the influx of various compounds, including several classes of antibiotics. Bacterial adaptation to reduce influx through porins is an increasing problem worldwide that contributes, together with efflux systems, to the emergence and dissemination of antibiotic resistance. Gram-negative bacteria are responsible for a large proportion of antibiotic-resistant bacterial diseases. These bacteria have a complex cell envelope that comprises an outer membrane and an inner membrane that delimit the periplasm (Pagès et al. 2008). Thus while addressing the issue of antibiotic resistance, enhancing the permeability of drugs is of fundamental importance.

Combined antibiotic therapy has been shown to delay the emergence of bacterial resistance and also produces desirable synergistic effects in the treatment of bacterial infections (Adwan and Mhanna 2008). Also in case of nanoparticles, when they are used together with antibiotics; advantage is conferred that if bacteria have resistance against one of the components, a further component could kill them in a different manner (Rai et al. 2010).

The sophorolipid combinations with one or more known antiviral agents or one or more known spermicidal agents to produce alternative antiviral agents and spermicidal agents reported in US 20120231068 (Gross, Richard A).

In the light of the above, there is a need in the art to develop en effective antibiotic composition that can be successfully used against antibiotic resistance. Further, it is evident that none of the prior art reports a synergistic pharmaceutical composition comprising sophorolipid in combination with an antibiotic.

OBJECTIVES OF THE INVENTION

The main objective of the present invention is to provide a synergistic pharmaceutical composition comprising a sophorolipid in combination with an antibiotic to effectively combat the antibiotic resistance in a subject, by increasing the permeability of the antibiotic drugs onto the outer membrane of bacteria.

Another objective of the present invention is a method of treating an infection selected from the group consisting of skin, intestinal and extra-intestinal comprising administering to a subject in need thereof an effective amount of pharmaceutical composition of the present invention.

SUMMARY OF THE INVENTION

Accordingly, the present invention provides a pharmaceutical composition comprising a sophorolipid in combination with an antibacterial agent and one or more pharmaceutical excipient, to effectively combat the antibiotic resistance in a subject by increasing the permeability of the antibiotic across the outer membrane of bacteria.

In an embodiment of the present invention, the concentration of sophorolipid and antibiotic is in the range of 10:1 to 20:1.

In one embodiment of the present invention, the antibacterial agent is selected from the group consisting of cephalosporin and tetracycline. Cephalosporin antibiotic used in the present invention is ceflacor and tetracycline antibiotic used in the present invention is tetracycline.

In another embodiment of the present invention, the concentration of the sophorolipid in the pharmaceutical composition is in the range of 10 mg to 2000 mg based on the amount of antibiotic used in the composition.

In an embodiment of the present invention the pharmaceutical excipient or carrier is selected from the group consisting of binder, filler, disintegrant, lubricant, glident, polymer, color, flavor and film coating agent.

In another embodiment of the present invention, the pharmaceutical composition is formulated into solid, liquid and gaseous dosage form. The solid dosage form is selected from the group consisting of tablet, capsule, caplet, granule, powder, the liquid dosage form is selected from the group consisting of syrup, solution, suspension, elixir, dry powder for suspension, parenteral preparation and the gaseous include aerosol preparation. Parenteral dosage form is selected from the group consisting of intravenous, intramuscular, intracutaneous, intradermal, intrauterine and intrarectal etc. Optionally the pharmaceutical composition may be administered in topical form or transdermal form. The topical composition include ointment, cream, gel, lotion. The pharmaceutical composition may also be administered as ophthalmic preparations.

The pharmaceutical composition of the invention may be prepared by conventional methods which are obvious to a person skilled in the art.

In an embodiment the present invention provides sophorolipid production and extraction and partial purification which were done according to the protocol mentioned in previous report using *Candida bombicola* ATCC 22214 (Joshi-Navare et al. 2011). Oleic acid was used as the fatty acid precursor. The SL sample was subjected to HPLC analysis to know about relative percentages of lactonic and acidic component using chromeline-Hitachi HPLC system with C18 column (5 µm, 150×4.6 mm). The acidic SL forms get eluted first while the lactonic SLs, especially the acetylated ones, show longer retention times because of higher hydrophobicity (Hu and Ju 2001). Thus, the peaks lying in the later half region were considered to be of different lactonic forms. The partially purified SL was found to contain around 75% of lactone form and remaining 25% of acidic form. However, the instant invention employs the SL mixture during the assay of conjugative effect with antibiotics assuming that natural synergism between SLs creates a better balance for many interfacial activities (Hirata et al. 2009).

In another embodiment the present invention provides a method of treating an infection comprising administering to a subject in need thereof an effective amount of a pharmaceutical composition comprising a sophorolipid, an antibiotic and one or more pharmaceutical excipient or carrier or diluent.

In an embodiment of the present invention, the infection is selected from the group consisting of skin, intestinal and extra-intestinal.

In an embodiment of the present invention, the effective amount of the pharmaceutical composition comprises administration of 250-500 mg of the antibiotic in combination with 500 mg-1 gm of the sophorolipid twice a day for one or two weeks.

BRIEF DESCRIPTION OF ACCOMPANYING DRAWINGS

FIG. 1: The sophorolipid increases the permeability of the antibiotic drugs onto the outer membrane of bacteria.

Figure 2:
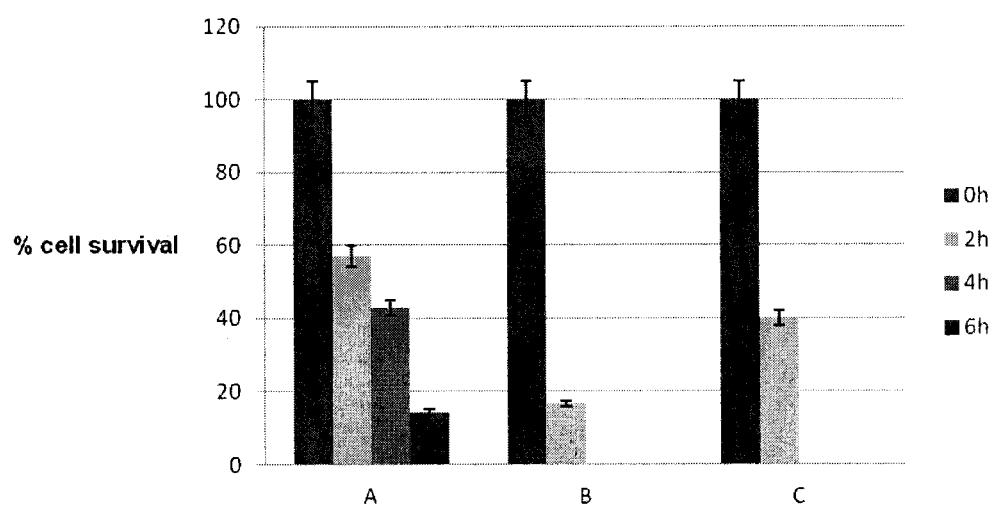
Figure 2B:
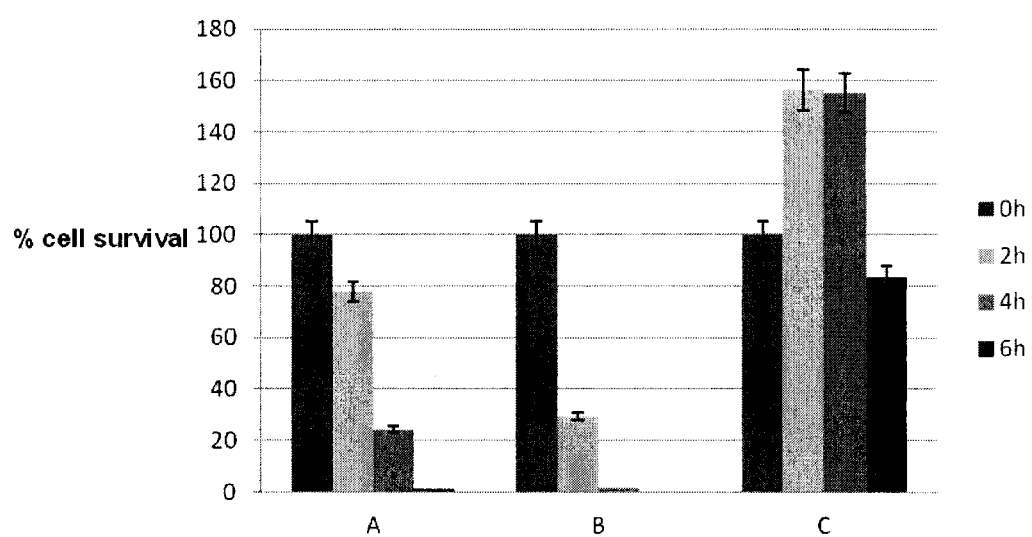

FIG. 2(*a*): The comparative inhibitory action of Tetracycline, SL and their combination against *Staphylococcus aureus* (Sublethal concentration of—Tetracycline is 15 µg/ml and sublethal concentration of SLOA is 300 µg/ml).

A: % cell survival on exposure to sublethal concentration of the antibiotic at periodic intervals B: % cell survival on exposure to combination of sublethal concentrations of the antibiotic and sophorolipid at periodic intervals C: % cell survival on exposure to sublethal concentration of the sophorolipid at periodic intervals FIG. 2(*b*): The comparative inhibitory action of Cefaclor, SL and their combination against *Escherichia Coli* (Sublethal concentration of Cefaclor is 50 µg/ml and sublethal concentration of SLOA is 500 µg/ml).

Figure 3:
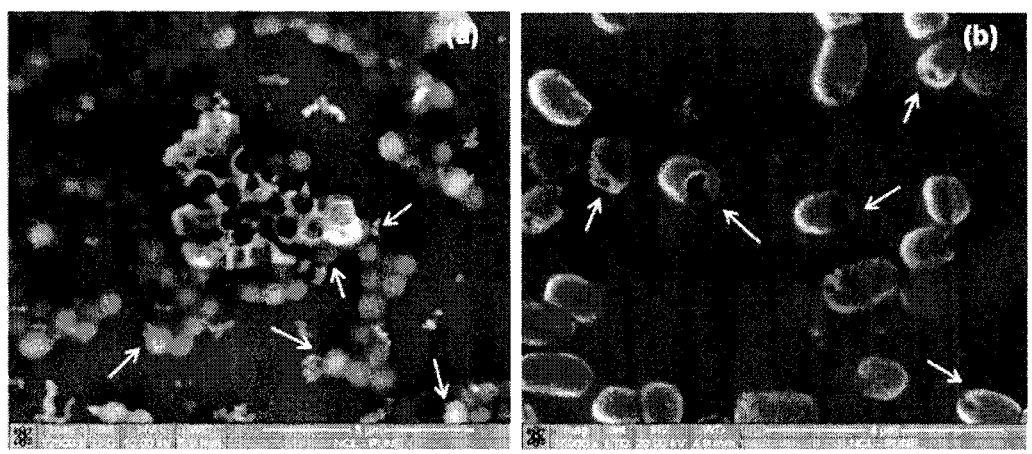

A: % cell survival on exposure to sublethal concentration of the antibiotic at periodic intervals B: % cell survival on exposure to combination of sublethal concentrations of the antibiotic and sophorolipid at periodic intervals C: % cell survival on exposure to sublethal concentration of the sophorolipid at periodic intervals FIG. 3: represents SEM images of morphological examination of the cells exposed to the SL-antibiotic mixtures.

DETAILED DESCRIPTION OF THE INVENTION

Accordingly, the invention provides a pharmaceutical composition comprising a sophorolipid in combination with an antibacterial agent and one or more pharmaceutical excipient or carrier or diluent, to effectively combat the antibiotic resistance in a subject by increasing the permeability of the antibiotic drugs onto the outer membrane of bacteria.

In an embodiment of the present invention, the concentration of sophorolipid and antibiotic is in the range of 10:1 to 20:1.

The antibacterial agent is selected from the group consisting of cephalosporin and tetracycline. Cephalosporin antibiotic used in the present invention is cefaclor while tetracycline antibiotic used in the present invention is tetracycline The pharmaceutical composition of the present invention may be formulated into any form which allows for the composition to be administered to a subject. For example, the composition may be in the form of a solid, liquid or gas (aerosol). The composition may be formulated into oral, topical, parenteral, transdermal, intravenous (IV), intramuscular, intracutaneous, intradermal, intrauterine and intrarectal or as an infusion. The pharmaceutical composition of the invention are formulated so as to allow the active ingredients contained therein to be bioavailable upon administration of the composition to a subject. The pharmaceutical composition may be formulated as per the conventional methods which are obvious to a person skilled in the art, using one or more pharmaceutical excipients. The pharmaceutical excipient/carrier is selected from the group consisting of binder, filler, disintegrant, lubricant, glidant, polymer, colour, flavour and film coating agent. The concentration of sophorolipid may vary from 10 mg to 2000 mg based on the amount of antibiotic used in the formulation and the concentration/dosage of antibiotic that may be used in the composition is well-established in the art.

The test microorganisms—*Staphylococcus aureus* (ATCC-29737) (gram positive) and *Escherichia coli* (ATCC-8739) (gram negative) used in the invention were procured from National Collection of Industrial Microorganisms, NCL. These two bacteria are of concern due to following reasons—*Staphylococcus aureus*, capable of causing wide range of severe skin infections; is rapidly evolving resistance to contemporary topical as well as systemic antibiotics (Englander and Friedman 2010). And *Escherichia coli*, another index bacterium; is more than just a harmless intestinal inhabitant; it can also be a highly versatile, and frequently deadly pathogen. Several different *E. coli* strains cause diverse intestinal and extra-intestinal diseases by means of virulence factors that affect a wide range of cellular processes (Kaper et al. 2004).

The present invention includes experimentation with *Escherichia coli* bacterium so as to observe the antimicrobial effect of cefaclor and cefaclor in combination with SL on the Gram negative bacteria that have a thin peptidoglycan layer adjacent to the inner cytoplasmic membrane which contributes to the resistance against cefaclor.

In an embodiment of the present invention, for testing the conjugative/synergistic action along with SL, the antibiotics, tetracycline, and cefaclor were chosen as both differ in their site of action. Tetracycline is the protein synthesis affecting antibiotic while cefaclor is the cell wall acting antibiotic.

Accordingly, the stock solutions were prepared in sterile distilled water to assess the MIC values of the antibiotic and SL. The stock strength used was 1 mg/ml for antibiotics and 10 mg/ml for SL. The conjugative/synergistic effect of SL and tetracycline was checked against *S. aureus* while the conjugative effect of SL and cefaclor was checked against *E. coli*. In the first step, $A_{600}$ i.e. absorbance of bacterial suspension giving isolated colonies was fixed and the same $A_{600}$ was maintained throughout the experiment. Then the MIC values were determined for SL as well as antibiotic against the bacteria. Minimum Inhibitory Concentration (MIC) is defined as the lowest concentration of compound that inhibits visible growth of microorganisms on the culture plate (Rai et al. 2010). For assessing the conjugative effect, the sublethal concentrations of both antimicrobial agents were used so as to rightly evaluate the conjugative effect. Against *S. aureus*, sublethal concentration of SL was decided to be 300 μg/ml and for tetracycline it was 15 μg/ml. In case of *E. coli*, based on the results of MIC determination experiment, the sub lethal concentrations of SL and Cefaclor were found to be 500 μg/ml and 50 μg/ml, respectively.

According to another aspect, the assay of conjugative action of SL and antibiotic was performed using standard micro dilution and spread plate method. The reaction mixtures were prepared by adding SL and antibiotic stock solutions to sterile distilled water in requisite volumes followed by the addition of bacterial suspension. The control reactions were also set with both bacterial systems to evaluate the effect of antibiotic and SL alone. Controls without addition of any antimicrobial agent were also maintained. The reaction mixtures were incubated at 28° C., 180 rpm for 6 h. The samples were removed at periodic intervals of 2 h, 4 h and 6 h and number of Colony Forming Units (CFUs) were determined by spreading 50 μl of mixture on Nutrient agar plates. The plates were incubated at 28° C. and colonies were visualized after 24 h. All antibacterial activity tests were performed in triplicates to certify the reproducibility. Colonies were counted and percentage cell survival was calculated using following formula (Gupta et al. 2012).

Percentage (%) cell survival=number of colonies on test plate×100/number of colonies on control plate.

The Percentage (%) cell survival data was plotted graphically with respect to time intervals. As is evident from FIG. 2(*a*), Tetracycline, the protein synthesis affecting antibiotic alone cannot achieve total inhibition even after 6 h of exposure whereas SL alone at 300 μg ml$^{-1}$ was efficient against *S. aureus* and showed total inhibition till 4 h. However, it was worth noting that when both agents were used in combination, at 2 h exposure ~22% more inhibition was observed.

FIG. 2(*b*) represents the comparative inhibitory action of cefaclor, SL and their combination against *E. coli*. Cefaclor, the cell wall synthesis affecting antibiotic has achieved almost total inhibition at the end of 6 h exposure. SL alone was totally unable to inhibit the bacterial growth but when administered along with the antibiotic; resulted in faster killing of the bacterium. It is worth to be noted that SL-cefaclor together could achieve ~98% killing within 4 h while with Cefaclor alone requires 6 h exposure to get equivalent effect.

In a further embodiment, the cells exposed to the SL-antibiotic mixtures were further subjected to morphological examination through Scanning electron microscopy (FIG. 3). The protocol used for sample preparation was as follows. Micro dilution assay was performed as mentioned before using a dense cell suspension ($A_{600}$=0.05) in order to ensure easier locating of bacterial cells. After 4 h incubation with SL-antibiotic combination, the bacterial cell suspension 10-15 μl was drop casted on to a silicon wafer and allowed to air dry. Samples were sputter coated till a fine layer of 10 nm was formed. (Sputter coater; make—EMITECH, source—Au—Pd, Gas-Argon). The E-SEMs of the samples were then recorded at the resolution 3 nm at 30 kV under high vacuum. (SEM; make—FEI, model-Quanta 200 #D Dual beam ESEM with EDAX, source—Tungsten thermionic emission). The untreated healthy cells prepared as described earlier were also subjected to SEM for reference.

Damage to cell membrane is evident with cells treated with SL-antibiotic mixture. The consequences of disturbed cell membrane integrity such as formation of membrane pores leading to leakage of cytoplasmic contents, accumulation of cell debris could also be noted. In the light of the mode of action observed from SEM images, it is obvious that the inhibitory action involves "cell membrane lipid order perturbation" in addition to the action of antibiotic.

In the light of the morphological examination through Scanning electron microscopy, the invention proposes mechanism of drug entry facilitation by the use of sophorolipids as shown in FIG. 1.

In the light of the foregoing, it is evident that the action is not merely additive because it requires large doses of the SLs to demonstrate any antibacterial activity, especially with Gram-negative bacteria as compared to Gram-positive bacteria (Sleiman et al. 2009). Also, in case of *E. coli*; SL alone cannot inhibit the bacterium but when co-administered with antibiotic achieves faster killing as compared to antibiotic alone. Therefore, it is clear that SLs have played a role in making the drug entry easier by disturbing the structure of cell membrane thereby enhancing the effect of antibiotic.

The SLs, on account of their amphiphilic nature, are capable of forming micelles, bilayer structures and self assemblies which can enclose the water soluble drugs. When administered together, SLs can span through the structurally alike cell membrane lipid bilayer and deliver the drug molecules to the cell interior, thus playing the role of drug delivery agent. SLs are known to have better antibacterial action against Gram positive bacteria while it requires large doses of the SLs to demonstrate any antibacterial activity, especially with Gram-negative bacteria. Therefore, the enhanced efficiency of Cefaclor-SL combination against *E. coli* can be considered as a proof of better performance due to facilitation of entry of drug molecules onto the outer membrane of bacteria by SLs.

Similarly SLs being antimicrobial in nature, it can be expected that when SL and antibiotic are co-administered, bacteria have to combat against 2 agents hence reducing the likelihood of bacterial survival as well as development of resistance.

EXAMPLES

Following examples are given by way of illustration therefore should not be construed to limit the scope of the invention.

Example 1

Preparation of Sophorolipids

The sophorolipid production and extraction and partial purification were done according to the protocol mentioned in previous report using *Candida bombicola* ATCC 22214 (Joshi-Navare et al. 2011). Oleic acid was used as the fatty acid precursor. The SL sample was subjected to HPLC analysis to know about relative percentages of lactonic and acidic component using chromeline-Hitachi HPLC system with C18 column (5 µm, 150×4.6 mm) The acidic SL forms get eluted first while the lactonic SLs, especially the acetylated ones, show longer retention times because of higher hydrophobicity (Hu and Ju 2001). Thus the peaks lying in the later half region were considered to be of different lactonic forms. The partially purified SL was found to contain around 75% of lactone form and remaining 25% of acidic form. However, the instant invention employs the SL mixture during the assay of conjugative effect with antibiotics assuming that natural synergism between SLs creates a better balance for many interfacial activities.

Example 2

Preparation of Stock Solutions

The stock solutions were prepared in sterile distilled water to assess the MIC values of the antibiotic and SL. The stock strength used was 1 mg/ml for antibiotics and 10 mg/ml for SL.

Example 3

Evaluation of MIC of Sophorolipid, the Antibiotic and the Synergistic Effect of the Combination Minimum Inhibitory Concentration (MIC) is defined as the lowest concentration of compound that inhibits visible growth of microorganisms on the culture plate (Rai et al. 2010).

a) Tetracycline MIC Against *Staphylococcus aureus*=150 µn/ml

SLOA (Sophorolipid derived from oleic acid) MIC against *Staphylococcus aureus*=400 µg/ml. For assessing the conjugative effect, the sublethal concentrations of both antimicrobial agents were used so as to rightly evaluate the conjugative effect. Against *S. aureus*; sublethal concentration of SL was decided as 300 µg/ml and for tetracycline it was 15 µg/ml. The comparative inhibitory action of Tetracycline, SL and their combination against *S. aureus* is shown in FIG. 2(*a*) and Table 1.

TABLE 1

SL-tetracycline combination performance assessment against *S. aureus*

MIC value of tetracycline-HCl against *S. aureus* (ATCC29737) = 150 µg/ml
MIC value of SL preparation against *S. aureus* (ATCC29737) = 400 µg/ml
Sublethal concentration of tetracycline-HCl = 15 µg/ml
Sublethal concentration of SL preparation = 300 µg/ml

| Inhibitory agents used | % cell survival on exposure to inhibitory agents at different time intervals | | | |
|---|---|---|---|---|
| | 0 h | 2 h | 4 h | 6 h |
| A (tetracycline-HCl alone) | 100 | 57.14 | 42.85 | 14.28 |
| B (tetracycline-HCl with SL) | 100 | 16.66 | 0 | 0 |
| C (SL alone) | 100 | 40 | 0 | 0 | b) Cefaclor MIC Against *Escherichia coli*=200 µg/ml

SLOA showed only little inhibitory action against *E. coli*.

In case of *E. coli*, based on the results of MIC determination experiment, the sub lethal concentrations of SL and Cefaclor were decided to be 500 µg/ml and 50 µg/ml, respectively. FIG. 2(*b*) and Table 2 represents the comparative inhibitory action of cefaclor, SL and their combination against *E. coli*.

TABLE 2

SL-cefaclor combination performance assessment against *E. coli*

MIC value of Cefaclor against *E. coli* (ATCC8739) = 200 µg/ml
MIC value of SL preparation against *E. coli* (ATCC8739) = No inhibitory action
Sublethal concentration of Cefaclor = 50 µg/ml
Sublethal concentration of SL preparation = 500 µg/ml

| Inhibitory agents used | % cell survival on exposure to inhibitory agents at different time intervals | | | |
|---|---|---|---|---|
| | 0 h | 2 h | 4 h | 6 h |
| A (cefaclor alone) | 100 | 77.89 | 24.21 | 1.05 |
| B (cefaclor with SL) | 100 | 29.56 | 1.7 | 0 |
| C (SL alone) | 100 | 156.4 | 155.22 | 83.87 |

As represented by the above figure, total inhibition has not been achieved in any of the test mixtures but maximum inhibition has been achieved in case of antibiotic-SLOA combination.

Example 4

Pharmaceutical Compositions

Based on the results of MIC and on the well-established doses of the antibiotics, any person skilled in the art may arrive at suitable dosage form that can give desired therapeutic/synergistic effect. For example, depending on the nature and severity of the infection an adult dose of 250-500 mg of tetracycline in combination with sophorolipid 1 gm may be taken orally twice a day for one or two weeks. Alternately equally divided doses may be taken to achieve the same effect. Similarly, paediatric doses may be arrived based on the body weight of the child as per methods known in the art.

Similarly, the combination of Cefaclor and sophorolipid may be formulated by any person skilled in the art may arrive at suitable dosage form that can give desired therapeutic/synergistic effect. For example, depending on the nature and severity of the infection an adult dose of 250-500 mg of cefaclor in combination with sophorolipid 500 mg to 1 gm may be taken orally twice a day for one or two weeks depending on the variety of symptoms to be treated. Alternatively equally divided doses may be taken to achieve the same effect. Similarly, paediatric doses may be arrived at based on the body weight of the child as per methods known in the art.

The compositions may be formulated using one or more pharmaceutical excipients in conventional dosage forms such as tablet, bilayer tablet, a tablet with a core coated by second active ingredient, granules filled in capsules, and such like. The tablets may be formulated in different release profiles to provide maximum therapeutic effect.

Also, the pharmaceutical composition may be administered in liquid and parenteral dosage forms. The preparation of dosage form may be known to a person skilled in the art using suitable excipients.

Further, the pharmaceutical composition may be administered as otic, and ophthalmic preparations.

ADVANTAGES OF THE INVENTION

Novel synergistic composition that can combat resistant bacteria.

Increased permeability of antibiotic drugs across the outer membrane of bacteria.

We claim:

1. A pharmaceutical composition comprising a sophorolipid, an antibiotic and one or more pharmaceutical excipient or carrier or diluent, to combat the antibiotic resistance in a subject, wherein the sophorolipid increases the permeability of the antibiotic onto the outer membrane of a bacterium, wherein the antibiotic is selected from cephalosporin or tetracycline, wherein said antibiotic is affecting cell wall or protein synthesis.

2. The pharmaceutical composition as claimed in claim 1, wherein the concentration of said sophorolipid and antibiotic is in the range of 10:1 to 20:1.

3. The pharmaceutical composition as claimed in claim 1, wherein the amount of sophorolipid is in the range of from 10 mg to 2000 mg based on the amount of antibiotic used in the composition.

4. The pharmaceutical composition as claimed in claim 1, wherein the pharmaceutical excipient or carrier is selected from the group consisting of binder, filler, disintegrant, lubricant, glident, polymer, color, flavor and film coating agent.

5. The pharmaceutical composition as claimed in claim 1, wherein the pharmaceutical composition is used in the form selected from the group consisting of tablet, capsule, caplet, granule, powder, syrup, solution, suspension, elixir, dry powder for suspension, parenteral preparation and aerosol.

6. A method of treating an infection caused by *Staphylococcus aureus* or gram negative bacteria comprising administering to a subject in need thereof an effective amount of a pharmaceutical composition comprising a sophorolipid, an antibiotic and one or more pharmaceutical excipient or carrier or diluent, wherein the antibiotic is selected from cephalosporin or tetracycline, wherein said antibiotic is affecting cell wall or protein synthesis.

7. The method of treating an infection caused by *Staphylococcus aureus* or gram negative bacteria as claimed in claim 6, wherein the infection is selected from the group consisting of skin, intestinal and extra-intestinal.

8. The method of treating an infection caused by *Staphylococcus aureus* or gram negative bacteria as claimed in claim 6, wherein the effective amount of the pharmaceutical composition comprises administration of 250-500 mg of the antibiotic in combination with 500 mg-1 gm of the sophorolipid twice a day for one or two weeks.

9. The method of treating an infection caused by *Staphylococcus aureus* or gram negative bacteria as claimed in claim 6, wherein the pharmaceutical composition is administered by a route selected from the group consisting of oral, topical, parenteral, transdermal, intravenous (IV), intramuscular, intracutaneous, intradermal, intrauterine, intrarectal and infusion.

* * * * *